(12) United States Patent
Mizuno

(10) Patent No.: US 7,192,425 B2
(45) Date of Patent: Mar. 20, 2007

(54) LASER TREATMENT APPARATUS

(75) Inventor: Katsuyasu Mizuno, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 184 days.

(21) Appl. No.: 10/972,358

(22) Filed: Oct. 26, 2004

(65) Prior Publication Data
US 2005/0096641 A1 May 5, 2005

(30) Foreign Application Priority Data
Oct. 31, 2003  (JP)  ............... 2003-372875

(51) Int. Cl.
*A61B 18/20* (2006.01)
*G02B 5/30* (2006.01)
(52) U.S. Cl. .............. 606/17; 606/4; 606/10; 606/18; 359/489; 359/495
(58) Field of Classification Search .......... 606/4–19; 351/205–215; 359/485–502
See application file for complete search history.

(56) References Cited

U.S. PATENT DOCUMENTS 4,836,203 A * 6/1989 Muller et al. .................. 606/3
5,208,699 A * 5/1993 Rockwell et al. ........... 359/338
5,226,903 A * 7/1993 Mizuno ........................ 606/17
6,574,015 B1 * 6/2003 Tselikov et al. .............. 398/36
2002/0133146 A1 * 9/2002 Telfair et al. ................... 606/5
2003/0007149 A1 1/2003 Yamamoto et al.

FOREIGN PATENT DOCUMENTS

| JP | A 05-196811 | * | 8/1993 |
| JP | A 10-328227 | | 12/1998 |
| JP | A 2003-15085 | * | 1/2003 |

* cited by examiner

*Primary Examiner*—A. Farah
(74) *Attorney, Agent, or Firm*—Oliff & Berridge, PLC

(57) ABSTRACT

A laser treatment apparatus comprises: an optical guiding body which guides a treatment laser beam omitted from a laser source; an irradiation optical system for irradiating the treatment beam guided by the optical guiding body; a first beam splitter placed in the irradiation optical system to split the treatment beam guided thereto; a photo-detector which detects output of one of the split treatment beams; and a depolarizer placed in an optical path between the optical guiding body and the first beam splitter to spatially disturb a polarization state of the guided treatment beam.

8 Claims, 6 Drawing Sheets

LASER TREATMENT APPARATUS

BACKGROUND OF THE INVENTION

1. Field of the Invention

The present invention relates to a laser treatment apparatus to perform treatment by irradiating a treatment laser beam emitted from a laser source to an affected area.

2. Description of Related Art

In general, a laser treatment apparatus to irradiate a treatment laser beam to an affected area includes an optical guiding body such as an optical fiber to guide the treatment beam from an apparatus main body containing a laser source, and an irradiation optical system to irradiate the treatment beam guided by the optical guiding body to the affected area. Further, an apparatus that has an irradiation optical system having a beam splitter that splits a treatment laser beam into transmission (a transmitted beam) and reflection (a reflected beam), and a photo-detector that receives one of the treatment beams split by the beam splitter in order to detect (monitoring) an output of the treatment beam has been proposed.

An optical fiber as an optical guiding body is convenient because it is flexible to some degree. However, when an optical guiding status is changed by moving the optical fiber (e.g., kinked, coiled, etc), a polarization status of a laser beam guided by (or outputted from) the optical fiber is also changed. A general beam splitter that can be manufactured easily has a polarization dependence that reflectances are different in the P- and S-polarized components of a laser beam. Thus, there is a problem that a result of detection (a result of monitoring) by the photo-detector is also changed by a change in the polarization status of the treatment beam.

SUMMARY OF THE INVENTION

The present invention has been made in view of the above circumstances and has an object to overcome the above problems and to provide a laser treatment apparatus capable of detecting (monitoring) an output of a treatment laser beam with high precision.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus comprising: an optical guiding body which guides a treatment laser beam emitted from a laser source; an irradiation optical system for irradiating the treatment beam guided by the optical guiding body; a first beam splitter placed in the irradiation optical system to split the treatment beam guided thereto; a photo-detector which detects output of one of the split treatment beams; and a depolarizer placed in an optical path between the optical guiding body and the first beam splitter to spatially disturb a polarization state of the guided treatment beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
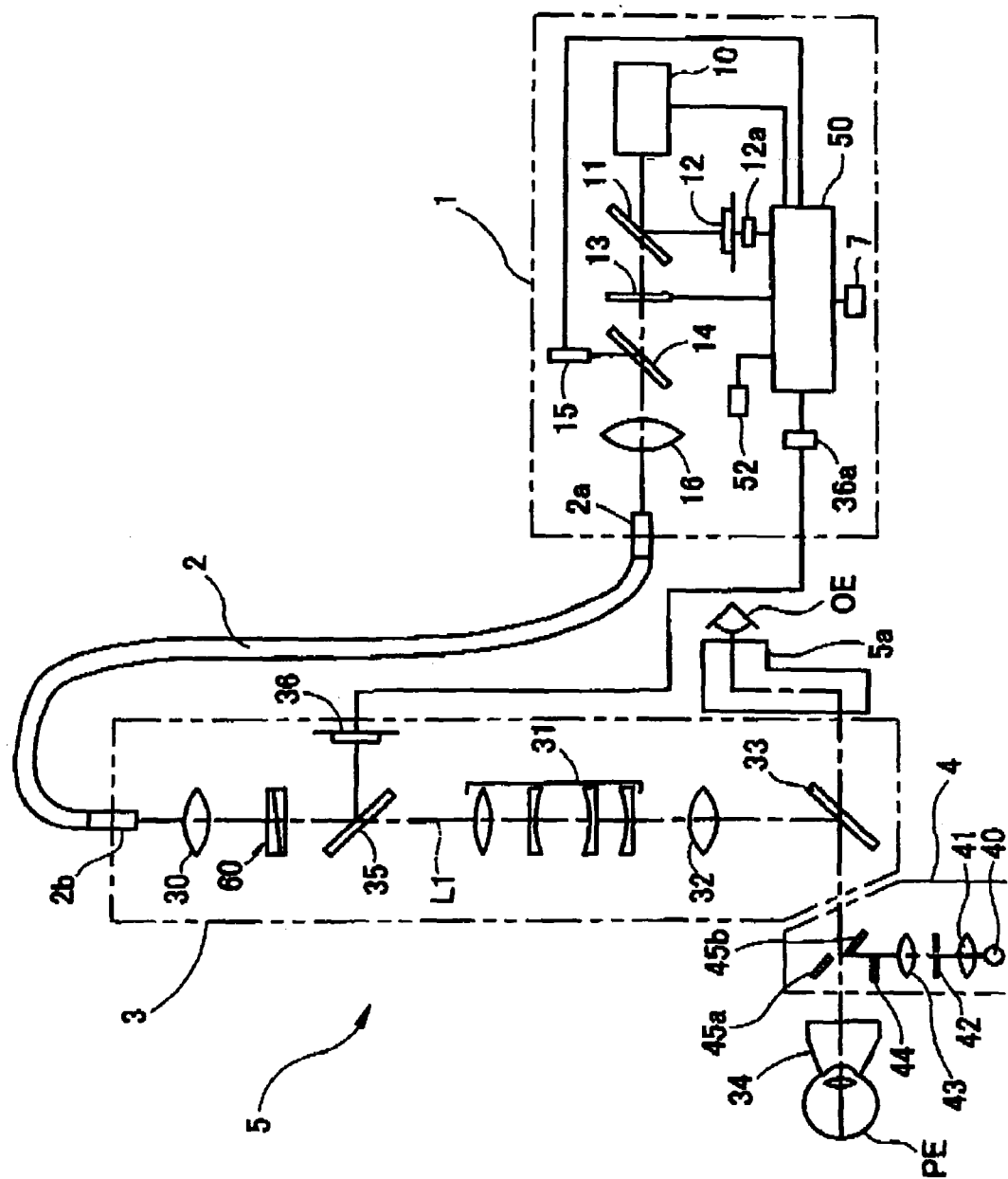
FIG. 1 is a schematic structural view of an optical system and a control system of an ophthalmic laser treatment apparatus.

An embodiment of the present invention will now be explained referring to the accompanied drawings. FIG. 1 is a schematic structural view of an optical system and a control system of an ophthalmic laser treatment apparatus according to the present invention.

A main body 1 of the apparatus includes a treatment laser source 10, an aiming laser source 15, an optical system to make a treatment laser beam (hereinafter, a treatment beam) and an aiming laser beam (hereinafter, an aiming beam) enter an optical fiber 2 as an optical guiding body and other components. A slit lamp delivery 6 is used to irradiate each beam on an affected area on an eye PE of a patient while allowing an operator to observe the eye PE. The slit lamp delivery 5 has an irradiation part 3, an illumination part 4, and a binocular microscope part (observation part) 5a. An optical fiber 2 guides each beam from the main body 1 to the irradiation part 3. Denoted by OE is an eye of the operator.

Most of the infrared treatment beam outputted from the laser source 10 passes through a beam splitter (half mirror) 11 and a residual small part of the treatment beam is reflected and split. The treatment beam reflected by the beam splitter 11 is received by a photo detector 12. Thus, the output of the treatment beam outputted from the laser source 10 is detected. When irradiation of the treatment beam is ready to be ordered, a safety shutter 13 is moved out of an optical path and allows the treatment beam to pass. In case of troubles as specified in advance, the safety shutter 13 is inserted into the optical path and blocks the treatment beam. The visible (red in this embodiment) aiming beam outputted from the laser source 15 is reflected by a dichroic mirror 14 and made to be coaxial with the treatment beam passing through the beam splitter 11. In other words, the dichroic mirror 14 has a property to pass the entire treatment beam and reflect the entire aiming beam. Each beam made to be coaxial is condensed and enters an incident end face 2a of the optical fiber 2 by a condenser lens 16. Meanwhile, the wavelengths of the treatment beam and the aiming beam are not limited to this embodiment.

The irradiation part 3 has an irradiation optical system including, orderly from the side of an emission end face 2b of the optical fiber 2, a relay lens 30, a depolarization plate 60 as a depolarizer, a beam splitter (half mirror) 35 that passes most of the treatment beam (and the aiming beam), and reflects and splits a residual small part of the treatment beam (and the aiming beam), a set of zoom lenses 31 movable in the direction of its optical axis in order to change the spot size of the treatment beam (and the aiming beam), an objective lens 32, and a dichroic mirror 33 that reflects the entire treatment beam and a part of the aiming beam and passes the other parts of the aiming beam. Further, in the reflective direction of the beam splitter 35, a photo-detector 86 is placed to detect the output of the treatment beam. Each optical component is arranged on an irradiation (guiding) optical axis L1 of the treatment beam (and the aiming beam).

It is to be noted that, in the present embodiment, the half mirror is used as the beam splitter 35. This is because the output of the aiming beam is extremely low as compared with that of the treatment beam and therefore has no effect on the photo-detector 36 in detecting the output of the treatment beam. As an alternative, the beam splitter 36 may be a dichroic mirror which allows the entire aiming beam and most of the treatment beam to pass therethrough and reflect a residual part of the treatment beam.

The treatment beam guided by the optical fiber 2 is made into a parallel beam by the relay lens 30, passes the depolarization plate 60, and is split by the beam splitter 35. The treatment beam having passed through the beam splitter 35 is reflected by the dichroic mirror 33 via the zoom lenses 31 and the objective lens 32. The treatment beam reflected by the dichroic mirror 33 and outputted from the irradiation part 3 is irradiated on an affected area of the eye PE through a contact lens 34. The treatment beam reflected by the beam splitter 35 is received by the photo-detector 36 and the output of the treatment beam is detected. Meanwhile, the aiming beam guided by the optical fiber 2 is irradiated on the affected area of the eye PE via the relay lens 30 through the contact lens 34.

At the illumination part 4, visible illumination light from an illumination light source 40 is made into parallel light by a condenser lens 41 and passes a slit of a slit plate 42. The illumination light that passed the slit of the slit plate 42 is reflected by split mirrs 45a and 45b via a projection lens 43, irradiated onto the eye PE through the contact lens 34. By this, the eye PE is illuminated by the slit light. A correction lens 44 corrects the length of the optical path of the illumination light reflected by the split mirror 45a.

The illumination light and aiming beam reflected by the eye PE partially pass through the dichroic mirror 33 and enters the microscope part 5a. This makes it possible for the eye OE to observe the affected area of the eye PE and the miming beam irradiated thereon.

Signals from the photo-detectors 12 and 36 are subjected to a predetermined process by detection processing circuits 12a and 36a respectively and inputted to a control part 50. Whether the optical guiding status of the optical fiber 2 is appropriate or not is judged by comparing the outputs of the treatment beam detected by the photo-detectors 12 and 36. When the optical guiding status of the optical fiber 2 is supposed to be abnormal, an alarm 52 sounds an alarm. In addition, a foot switch 7 to input a trigger signal to irradiate the treatment beam is connected to the control part 50.

Figure 2A:
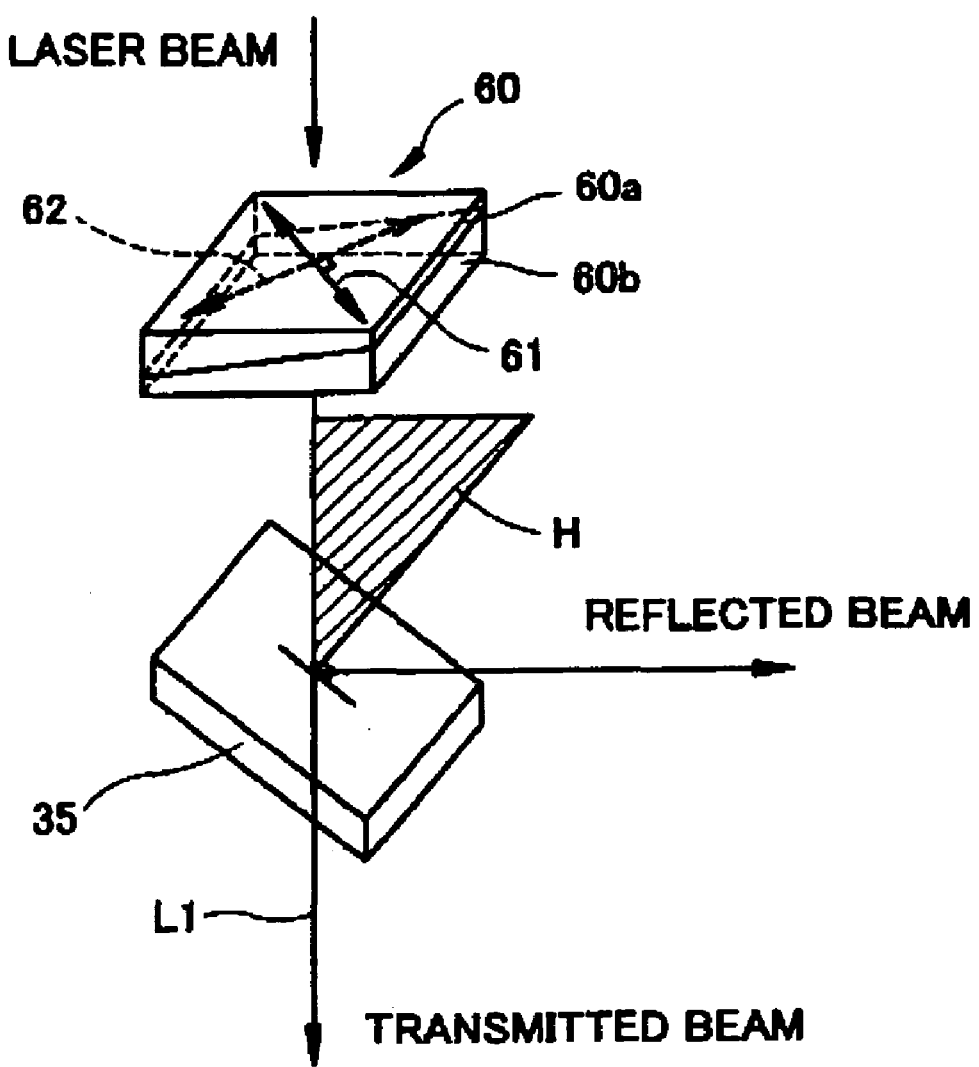
FIG. 2A is an explanatory view showing a depolarization plate and a beam splitter.
Figure 2B:
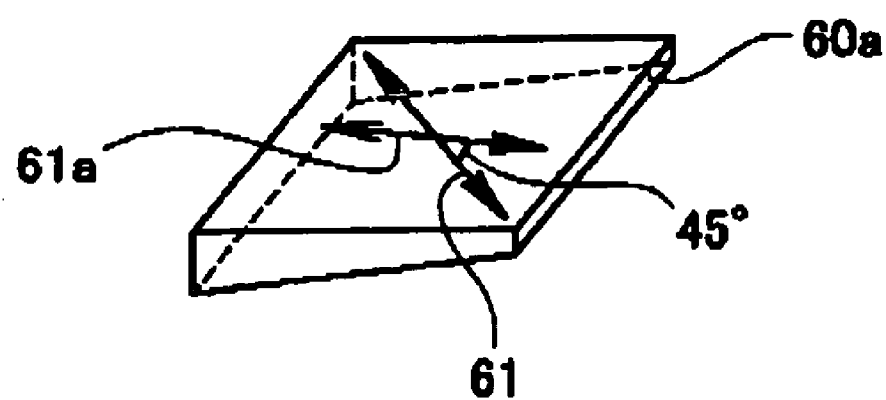
FIG. 2B is an exploded view of the depolarization plate of FIG. 2A.
Figure 2B:
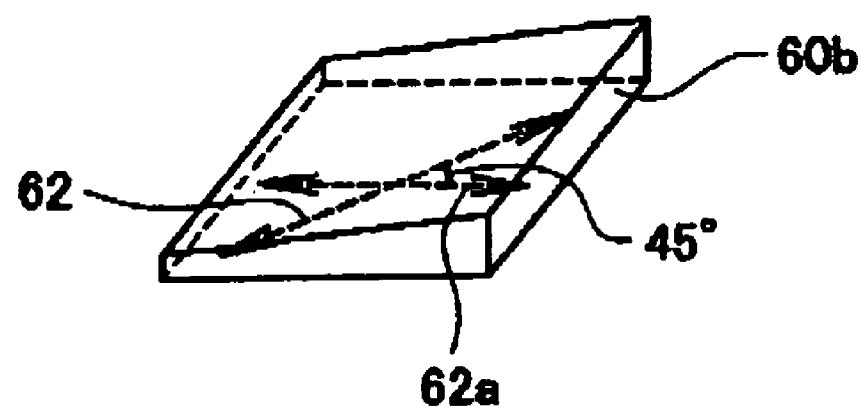
Figure 4:
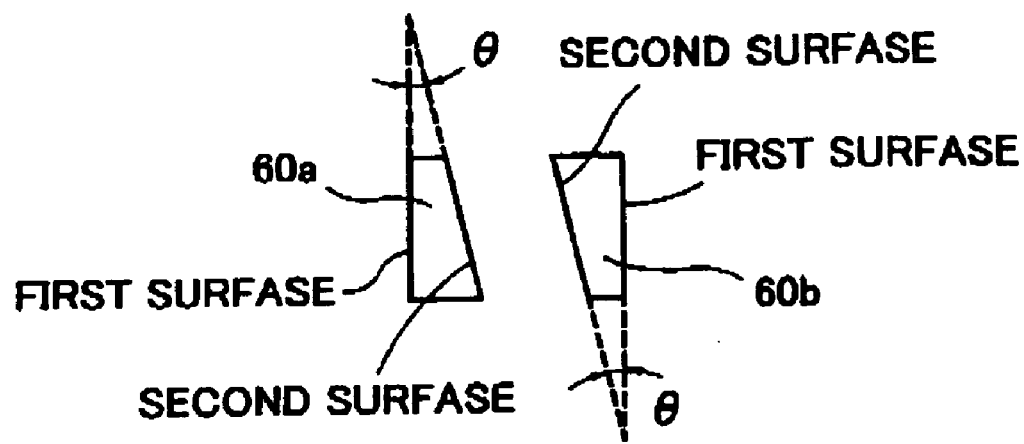
FIG. 4 is an explanatory view showing the depolarization plate.

The depolarization plate 60 and beam splitter 35 will now be explained referring to FIGS. 2A and 2B, and 4. The depolarization plate 60 is composed of two quartz plates 60a and 60b. The quartz plate 60a is formed to have a first surface (horizontal plane) including an optic axis 61 and a second surface (inclined plane) whose thickness varies continuously in the direction (indicated by an arrow 61a in FIG. 2B) at 45° with the optic axis 61. Meanwhile, the quartz plate 60b is formed to have a first surface (horizontal plane) including an optic axis 62 and a second surface (inclined plane) whose thickness varies continuously in the direction (indicated by an arrow 62a in FIG. 2B) at 45° with the optic axis 62. That is to say, the quartz plates 60a and 60b are identical. The depolarization plate 60 where the optic axes 61 and 62 are orthogonalized to each other and the directions of thickness variations of the quartz plates 60a and 60b are reverse (contrary) to each other (see FIG. 2A) is formed by overlapping and attaching the second surface of the quartz plate, 60a to the second surface of the quartz plate 60b (see FIG. 4). The directions of the continuous thickness variations of the quartz plates 60a and 60b to the optic axes 61 and 62 are arbitrary. However, if the directions are set at an angle of 45° with the optic axes 61 and 62, the quartz plate 60a and the quartz plate 60b identical in structure may be used.

In the depolarization plate 60 with this configuration, the phases to be provided vary according to the places through which light passes because the quartz plates 60a and 60b are different in thickness depending on the place through which light passes. Therefore, the depolarization plate 60 can change the polarization state of light into a state where many polarization states are mixed spatially. In other words, the polarization state is spatially disturbed. However, the depolarization plate 60 has no effect on the linear polarized light that is parallel or perpendicular to each optic axes 61 and 62. Therefore, this linear polarized light is allowed to pass without any disturbances.

The beam splitter 35 has a property to pass most of the treatment beam and reflects a residual small part of the treatment beam. In the present embodiment, the beam splitter 35 is a common glass plate applied with a single layer antireflection coating made of magnesium fluoride, which has a polarization dependence where reflectance Rs of the S-polarized component and the P-polarized component are different. For example, if the incident angle of the treatment beam is 45°, the reflectance Rs of the P-polarized component is 3.853%, the reflectance Rp of the P-polarized component is 0.110%, and the ratio Ra/Rp is 35. At this moment, the depolarization plate 60 transmits the linear polarized light parallel or perpendicular to the optic axes 61 and 62 as it is. Therefore, the beam splitter 35 is arranged so that a plane H including the irradiation (incident) optical axis L1 of the treatment beam and the normal of the reflection plane of the beam splitter 35 is misaligned with the optic axes 61 and 62. Preferably, the beam splitter 35, is arranged so that each of the optic axes 61 and 62 makes an angle of 45° with the plane H.

The treatment beam guided by the optical fiber 2 is converted by the depolarization plate 60 into a state where many polarization states are mixed, reflected by the beam splitter 35 and received by the photo-detector 36 to detect the output. At this moment, with the configuration shown above, even if the polarization state of the treatment beam guided by the optical fiber 2 is changed, changes in the light amount of the treatment beam reflected by the beam splitter 35 are suppressed because the depolarization plate 60 eliminates the polarization state. Thus, the photo-detector 36 can detect the output of the treatment beam in a stable and accurate manner.

Figure 3:
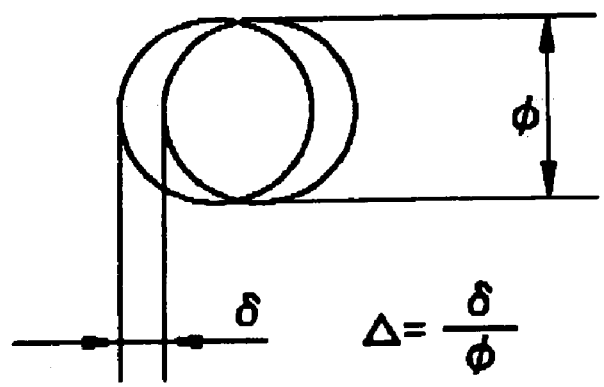
FIG. 3 is an explanatory view showing an image of an emission end face of an optical fiber on a target surface by quartz (crystal) birefringence.

When using the depolarization plate 60 shown above, the image of the emission end face 2b of the optical fiber 2 on a target surface is misaligned to the direction of the thickness variations of the quartz plates 60a and 60b, generating a double image as shown in FIG. 3. Supposing that the ratio of a discrete quantity δ to a spot diameter φ is a separation degree Δ, the separation degree Δ is proportional to the angle θ made by the first and second surfaces of the quartz plate 60a (or the quartz plate 60b), and the focal length of the lens 30. Meanwhile, the depolarizing effect of the depolarization plate 60 is also proportional to the angle θ made by the first and second surfaces of the quartz plate 60a (or the quartz plate 60b), and the focal length of the lens 30. A smaller separation degree Δ and a larger depolarizing effect are contradictory to each other. Therefore, the angle θ must be determined so that the separation degree Δ is smaller enough from a practical standpoint and the depolarizing effect is larger. In this embodiment, when the focal length of the lens 30 is 32.4 mm and the separation degree Δ is 3.5%, the angle θ is 45' (minute). The separation degree Δ on the target surface is preferably 5% or less.

The separation degree Δ is obtained by adding the separation degree ½Δ given by the quartz plate 60a with the inclination of the second surface to the first surface of the quartz plate 60a and the separation degree ½Δ given by the quartz plate 60b with the inclination of the second surface to the first surface of the quartz plate 60b.

Figure 5:
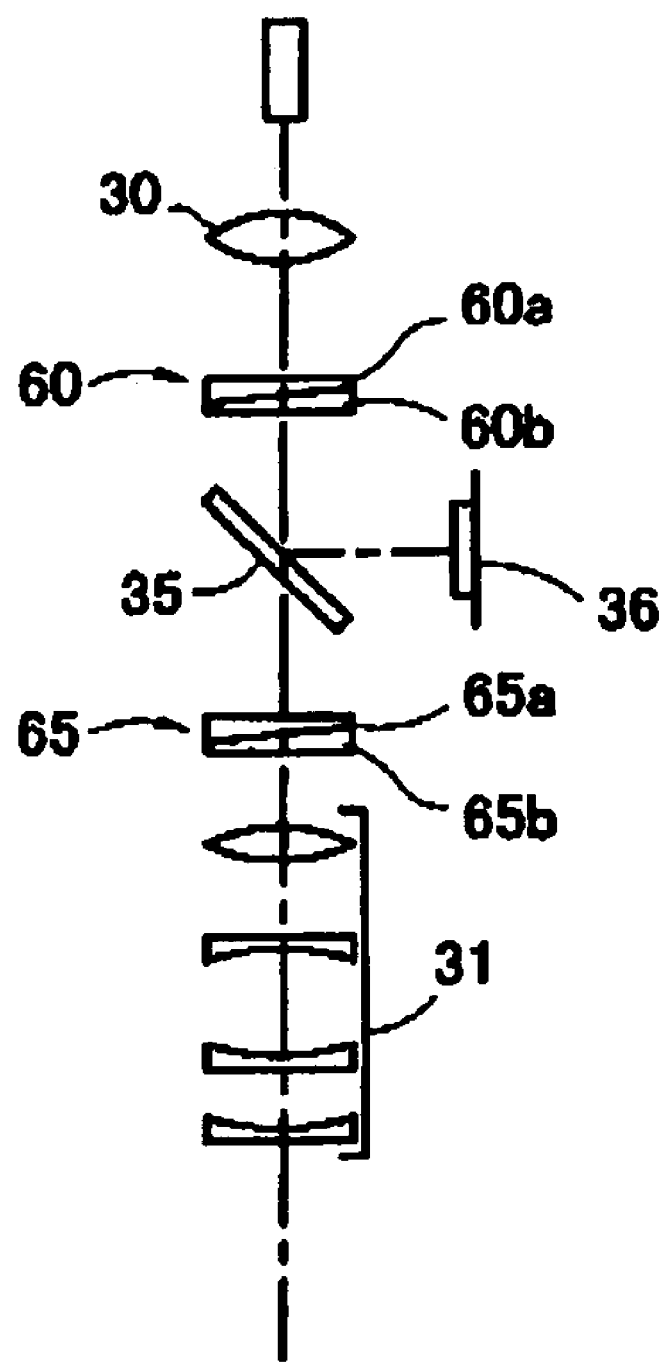
FIG. 5 is a schematic structural view of a main part of an irradiation optical system in a modified example.

A modification of this invention will now be explained. FIG. 5 is a schematic structural view of a main part of an irradiation optical system in a modification example. In this example, in contrast with the previous example (FIG. 1), a second depolarization plate 65 is disposed at the target surface side of the beam splitter 35 (between the beam splitter 35 and the objective lens 32) to compensate birefringence caused by the depolarization plate 60.

The depolarization plate 65 is disposed between the beam splitter 35 and the zoom lenses 31. As the depolarization plate 60, the depolarization plate 65 is composed of a quartz plate 65a (the direction of thickness variation is the same as the quartz plate 60a) on the side of the optical fiber 2 and a quartz plate 65b (the direction of thickness variation is the same as the quartz plate 60b) on the side of the target surface. The two quartz plates 65a and 65b are overlapped and attached in such a manner that the two optic axes are orthogonal to each other and the directions of thickness variations are reverse (contrary) to each other. However, contrary to the depolarization plate 60, the quartz plates 65a and 65b have the optic axes 62 and 61 respectively.

The single-layer antireflection coating made of magnesium fluoride is applied on the both sides of the beam splitter 35. Therefore, the phase difference between the S- and P-polarized components of the passing treatment beam is small (less than 1'). Thus, the birefringence by the depolarization plate 60 and the birefringence by the depolarization plate 65 cancel each other to prevent the image of the emission end face 2b of the optical fiber 2 on the target surface from being doubled as shown in FIG. 3.

Thus, the birefringence by the depolarization plate 60 can be eliminated by disposing the second depolarization plate 65 to enlarge the angle θ made by the first and second surfaces of each of the quartz plates 60a and 6b and achieve increased effectiveness of depolarization.

The depolarization plate 65 to compensate the birefringence by the depolarization plate 60 may be composed of the quartz plate 65a having the optic axis 61 with the direction of the thickness variation being the same as the quartz plate 60b, the quartz plate 65b having the optic axis 62 with the direction of the thickness variation being the same as the quartz plate 60a.

Figure 6:
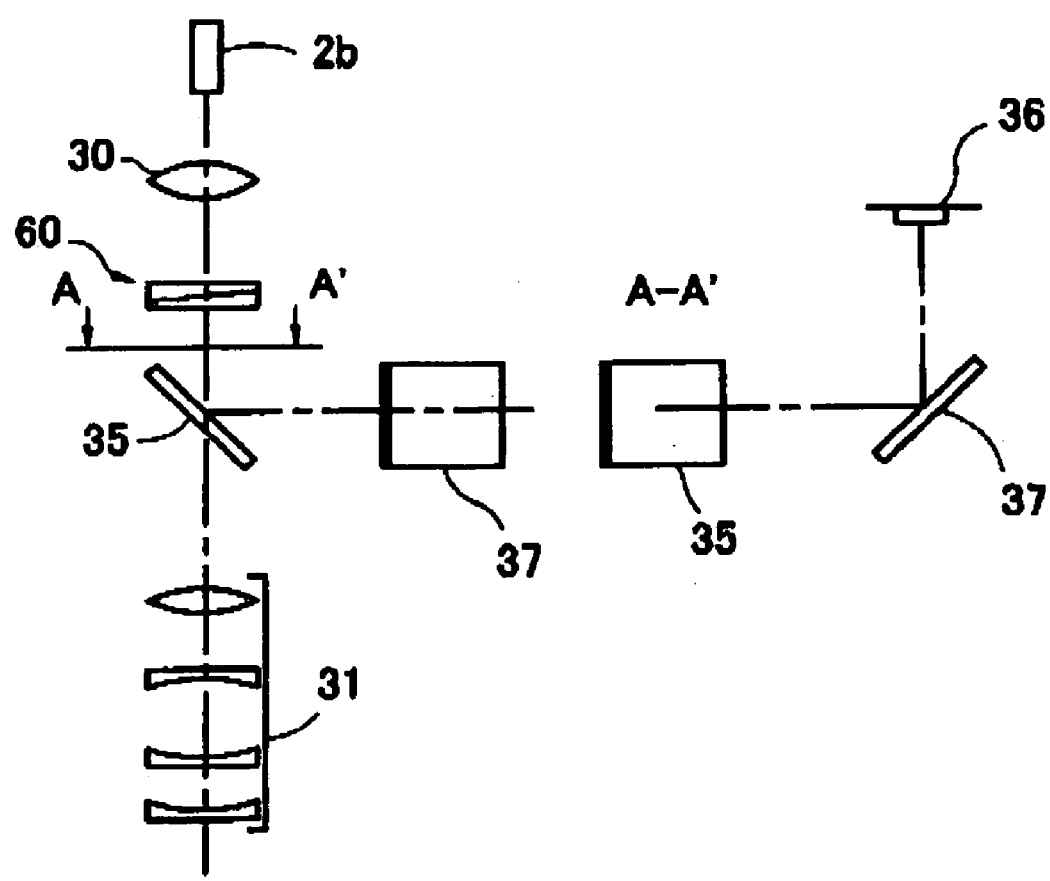
FIG. 6 is a schematic structural view of a main part of an irradiation optical system in another modified example.

Further, another modified example of the present invention will now be explained. FIG. 6 is a schematic structural view of a main part of an irradiation optical system in another modified example. In this example, in contrast with the previous example (FIG. 1), a second beam splitter 37 is disposed at the reflection side of the beam splitter 35 (between the beam splitter 35 and the photo-detector 36).

The beam splitter 37 is identical to the beam splitter 35, but different therefrom in placement status only. The beam splitter 37 is placed in a 90° rotated position with respect to the beam splitter 35 so that the directions of the P- and S-polarized components with respect to the beam splitter 35 and those with respect to the beam splitter 37 are exactly reverse (contrary) each other. Thus, the difference between the reflectances of the P- and S-polarized components by the beam splitter 37 eliminates the difference between the reflectances of the P- and S-polarized components by the beam splitter 35 to suppress the output variations of the treatment beam detected by the photo-detector 36.

As mentioned above, the addition of the beam splitter 37 eliminates the polarization dependence of the treatment beam entering the photo-detector 36 to thereby suppress the output variations of the treatment beam detected by the photo-detector 36. However, when manufacturing an apparatus actually, the beam splitter is preferably combined with the depolarization plate 60 because the beam splitter is sensitive to the slight differences of an irradiating direction of the treatment beam and the positional relationship between the traveling direction of a treatment beam and the beam splitters 35 and 37. This can enhance the effect to suppress the output variations due to the changing the polarization state of the treatment beam, allowing more accurate detections (monitoring) of outputs.

Above shown are examples of the ophthalmic laser treatment apparatus. This invention can also be applied to other medical laser apparatuses such as the one used in dermatology. There are multi-joint arms with many mirrors as an optical guiding body. With the multi-joint arms, accurate detections (monitoring) of treatment beams can be achieved by applying this invention.

In the embodiments described above, quartz plates are used for crystal plates constituting the depolarization plate 60. However, crystal plates made of crystals of magnesium fluoride may be used.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus comprising:
   a laser source;
   an optical guiding body which guides a treatment laser beam emitted from the laser source;
   an irradiation optical system for irradiating the treatment beam guided by the optical guiding body;
   a first beam splitter placed in the irradiation optical system to split the treatment beam guided thereto, the first beam splitter having a predetermined polarization dependence such that reflectances are different in P- and S-polarized components of the treatment beam;
   a depolarizer placed in an optical path between the optical guiding body and the first beam splitter to spatially disturb a polarization state of the guided treatment beam, the depolarizer eliminating a change in the polarization state of the guided treatment beam due to a change in optical guiding state of the optical guiding body; and
   a first photo-detector which detects output of one of the treatment beams split by the first beam splitter after passing through the depolarizer.

2. The laser treatment apparatus according to claim 1, further comprising:

a second beam splitter placed in an optical path between the laser source and the optical guiding body to split the emitted treatment beam;

a second photo-detector which detects output of one of the treatment beams split by the second beam splitter; and a control part which compares a detection result by the first photo-detector and a detection result by the second photo-detector.

3. The laser treatment apparatus according to claim 2, wherein the control part determines whether the optical guiding state of the optical guiding body is appropriate or not based on a comparison result.

4. The laser treatment apparatus according to claim 1, wherein the optical guiding body is an optical fiber.

5. A laser treatment apparatus comprising:

an optical guiding body which guides a treatment laser beam emitted from a laser source;

an irradiation optical system for irradiating the treatment beam guided by the optical guiding body;

a beam splitter placed in the irradiation optical system to split the treatment beam guided thereto;

a photo-detector which detects output of one of the split treatment beams; and a depolarizer placed in an optical path between the optical guiding body and the beam splitter to spatially disturb a polarization state of the guided treatment beam, wherein the depolarizer is formed of a first crystal plate having a first optic axis and a thickness varying continuously in a direction of any given angle with the first optic axis, and a second crystal plate having a second optic axis and a thickness varying continuously in a direction of any given angle with the second optic axis, the first and second crystal plates are overlapped and attached so that the first and the second optic axes are orthogonal to each other and the directions of the variations in thickness of the first and second crystal plates are opposite to each other;

the beam splitter is positioned so that a plane H which includes a normal of a reflection plane of the beam splitter and an incident optical axis of the treatment beam is in a positional relationship misaligned with the first and second optic axes; and the photo-detector is positioned on an opposite side of the first beam-splitter.

6. The laser treatment apparatus according to claim 5, wherein the thickness of the first crystal plate varies in a direction of 45° with the first optic axis;

the thickness of the second crystal plate varies in a direction of 45° with the second optic axis; and the beam splitter is positioned so that the plane H is in the positional relationship of 45° with the first and the second optic axes.

7. A laser treatment apparatus comprising:

an optical guiding body which guides a treatment laser beam emitted from a laser source;

an irradiation optical system for irradiating the treatment beam guided by the optical guiding body;

a beam splitter placed in the irradiation optical system to split the treatment beam guided thereto;

a photo-detector which detects output of one of the split treatment beams;

a depolarizer placed in an optical path between the optical guiding body and the beam splitter to spatially disturb a polarization state of the guided treatment beam; and a compensating member placed in an optical path between the beam splitter and an objective lens of the irradiation optical system to compensate birefringence generated by the depolarizer.

8. A laser treatment apparatus comprising:

an optical guiding body which guides a treatment laser beam emitted from a laser source;

an irradiation optical system for irradiating the treatment beam guided by the optical guiding body;

a first beam splitter placed in the irradiation optical system to split the treatment beam guided thereto;

a photo-detector which detects output of one of the split treatment beams;

a depolarizer placed in an optical path between the optical guiding body and the first beam splitter to spatially disturb a polarization state of the guided treatment beam; and a second beam splitter placed in an optical path between the first beam splitter and the photo-detector to make directions of a P- and S-depolarized components of one of the split treatment beams with respect to the first beam splitter and those with respect to the second beam splitter completely opposite to each other.

* * * * *